US00PP31406P2

(12) United States Plant Patent
Sheehan

(10) Patent No.: US PP31,406 P2
(45) Date of Patent: Jan. 28, 2020

(54) GRAPEVINE PLANT NAMED 'SHEEGENE 101'

(50) Latin Name: *Vitis vinifera*
Varietal Denomination: Sheegene 101

(71) Applicant: Sheehan Genetics Australia PTY, Ltd., Mildura (AU)

(72) Inventor: Timothy P. Sheehan, Vancouver, WA (US)

(73) Assignee: Sheehan Genetics Australia PTY, Ltd., Mildura (AU)

( * ) Notice: Subject to any disclaimer, the term of this patent is extended or adjusted under 35 U.S.C. 154(b) by 0 days.

(21) Appl. No.: 16/350,750

(22) Filed: Jan. 2, 2019

(51) Int. Cl.
*A01H 6/88* (2018.01)
*A01H 5/08* (2018.01)

(52) U.S. Cl.
USPC ..... Plt./205

(58) Field of Classification Search
USPC ..... Plt./205
CPC ..... A01H 5/08; A01H 6/88
See application file for complete search history.

(56) References Cited

U.S. PATENT DOCUMENTS

| | | | |
|---|---|---|---|
| PP4,787 | P | 11/1981 | Olmo |
| PP17,211 | P2 | 11/2006 | Gargiulo |
| PP17,504 | P3 | 3/2007 | Maranto |
| PP17,875 | P3 | 7/2007 | Gargiulo |
| PP18,226 | P3 | 11/2007 | Gargiulo |
| PP18,959 | P2 | 6/2008 | Sheehan |
| PP18,960 | P2 | 6/2008 | Sheehan |
| PP18,987 | P2 | 6/2008 | Sheehan |
| PP19,041 | P2 | 7/2008 | Sheehan |
| PP19,599 | P2 | 12/2008 | Maranto |
| PP19,911 | P2 | 4/2009 | Sheehan |
| PP19,912 | P2 | 4/2009 | Sheehan |
| PP20,110 | P3 | 6/2009 | Sheehan |
| PP20,236 | P3 | 8/2009 | Sheehan |
| PP20,252 | P3 | 9/2009 | Sheehan |
| PP20,281 | P3 | 9/2009 | Sheehan |
| PP20,317 | P3 | 9/2009 | Sheehan |
| PP20,753 | P3 | 2/2010 | Sheehan |
| PP21,075 | P2 | 6/2010 | Maranto |
| PP21,316 | P3 | 9/2010 | Sheehan |
| PP23,125 | P2 | 10/2012 | Sheehan |
| PP23,478 | P3 | 3/2013 | Chimenti |
| PP23,837 | P3 | 8/2013 | Sheehan |
| PP25,095 | P3 | 11/2014 | Sheehan |
| PP25,131 | P3 | 12/2014 | Sheehan |
| PP26,179 | P3 | 12/2015 | Sheehan |
| PP26,300 | P3 | 1/2016 | Lombard |
| PP28,269 | P3 | 8/2017 | Sheehan |
| PP29,129 | P2 | 3/2018 | Sheehan |
| 2008/0201809 | P1 | 8/2008 | Sheehan |
| 2013/0276181 | P1 | 10/2013 | Sheehan |
| 2016/0044845 | P1 | 2/2016 | Sheehan |

OTHER PUBLICATIONS

U.S. Appl. No. 16/350,751, filed Jan. 2, 2019, Sheehan.
U.S. Appl. No. 16/350,752, filed Jan. 2, 2019, Sheehan.
Application for Plant Breeder's Rights for Grapevine ( *Vitis vinifera*) Variety Sheegene 101, Australia, PBR No. 2019/024, filed Feb. 20, 2019.
Variety specific information as indicated in transmittal letter of Information Disclosure Statement for U.S. Appl. No. 16/350,750, filed May 8, 2019.

*Primary Examiner* — Annette H Para
(74) *Attorney, Agent, or Firm* — Dentons US LLP

(57) ABSTRACT

'Sheegene 101' is a new grapevine plant with novel characteristics that include good fertility and naturally loose bunches. The berries produced by 'Sheegene 101' are black and seedless with a crisp texture and no detectable seed traces. The berries produced by 'Sheegene 101' are large, weighing 7-8 g/berry on average, and are harvested in late August.

1 Drawing Sheet

Latin name of the genus and species of the plant claimed: *Vitis vinifera.*

Cultivar denomination: 'Sheegene 101'.

BACKGROUND OF THE INVENTION

The present invention relates to a new distinct variety of seedless grapevine named 'Sheegene 101'. The variety originated from a hybridization performed in Mildura, Victoria, Australia during 2002 between 'Crimson Seedless' (unpatented), as the pollen parent, and 'Autumn Royal' (unpatented), as the seed parent. Abortive seed traces were embryo cultured and the resulting plant was planted in an evaluation block during 2004. The first evaluation of the fruit produced by 'Sheegene 101' was performed during 2007. 'Sheegene 101' was first asexually propagated by field grafting dormant hardwood scions to rootstock in 2010 in Irymple, Victoria, Australia. Fruit from the resulting four grafted 'Sheegene 101' vines was first harvested in 2012. All characteristics and distinctions remain true to form and are established and transmitted through succeeding propagations.

SUMMARY OF THE INVENTION

The following are the most outstanding and distinguishing characteristics of 'Sheegene 101'. 'Sheegene 101' produces large, black (5RP 3/2), seedless berries that are harvested in late August and weigh on average 7-8 g/berry.

'Sheegene 101' can be distinguished from its male parent, 'Crimson Seedless', based at least upon berry color and weight and cluster weight. 'Sheegene 101' produces black berries; whereas, 'Crimson Seedless' produces red berries (2.5R 5/10). The weight of the berries produced by 'Sheegene 101' (7.7 g/berry on average) is greater than those of 'Crimson Seedless' (4.0 g/berry on average).

'Sheegene 101' can be distinguished from its female parent, 'Autumn Royal', based at least upon vigor, berry shape and attachment, rudimentary seeds per berry, bunch size, and fertility. 'Sheegene 101' displays a medium to high vigor; whereas; 'Autumn Royal' displays medium to low vigor. 'Sheegene 101' berries exhibit a datiform shape; whereas, 'Autumn Royal' berries exhibit an ovoid to ellipsoidal shape. The berries of 'Sheegene 101' are more strongly attached than those of 'Autumn Royal'. The berries of 'Autumn Royal' also exhibit 2-4 detectable rudimentary (aborted) seeds that each weigh about 7.2 mg. Any rudimentary seeds within the berries of 'Sheegene 101' are undetectable. The berry bunches produced by 'Sheegene 101' are smaller than those of 'Autumn Royal'. 'Sheegene 101' displays higher fertility than 'Autumn Royal'. The berries of 'Sheegene 101', however, exhibit the same crispy texture as those of 'Autumn Royal'.

'Sheegene 101' is harvested in August, which is earlier than the late September to early November harvest period of both 'Crimson Seedless' and 'Autumn Royal'.

BRIEF DESCRIPTION OF THE DRAWING

'Sheegene 101' is illustrated by the accompanying photograph, which shows the form, foliage, and fruit of a 4-year-old vine grown in the field at Murcia, Spain. The colors shown are as true as can be reasonably obtained by conventional photographic procedures.

DETAILED BOTANICAL DESCRIPTION

The following detailed description sets forth the distinctive characteristics of 'Sheegene 101'. The detailed description was obtained between March and November using 4-year-old plants grown in the field at Murcia, Spain. The color references are to the *Munsell Plant Tissue Color Book,* 2012 Edition by Munsell Color.

Classification:
- *Family.*—Vitaceae.
- *Botanical.*—*Vitis vinifera.*
- *Common name.*—Grapevine.
- *Cultivar name.*—'Sheegene 101'.

Plant:
- *Plant habit and growth.*—Semi-erect.
- *Age at maturity.*—4 years old.
- *Size* (*at maturity*).—Height: 225 cm. Width: 300 cm.
- *Vigor.*—Medium to high.
- *Productivity.*—High.
- *Rootstock.*—Name of rootstock: 1103 Paulsen Rootstock. Age of rootstock at time of grafting: one year old.

Trunk:
- *Size.*—Diameter: 7.1 cm.
- *Surface texture.*—Smooth.
- *Bark color.*—Exterior: 5YR 5/2. Interior: 5Y 7/6.

Canes:
- *Size.*—Diameter: 10 mm. Length: 200 cm.
- *Surface texture.*—Mature cane: smooth and finely ribbed. Immature cane: smooth and very finely ribbed.
- *Form* (*woody shoot cross section form*).—Pith in center with diaphragm at the nodes.
- *Color.*—Mature: 2.5Y 8/4 at 5 months. Immature: 5GY 7/8 at 4 weeks.
- *Internode length* (*upper mature sun cane*).—11.1 cm (on June 15).

Time of Bud Burst: 50% bud break by March 21.

Tendrils:
- *Form.*—Mostly trifid and bifid, curly.
- *Size.*—Medium.
- *Length.*—21.9 cm.
- *Diameter.*—2.8 mm.
- *Texture and distribution.*—Smooth and discontinuous; 00000110011011011.
- *Color.*—Mature: 2.5GY 6/8 at 4 weeks. Immature: 2.5GY 7/8 at 10 days.
- *Anthocyanin.*—Mature: absent. Immature: absent.

Growing Tips (Young Shoot):
- *Pubescence.*—Absent but with light cobweb.
- *Color.*—2.5GY 7/6.
- *Anthocyanin.*—Present, 5R 5/10.
- *Shape.*—Fully open.
- *Apex.*—Triangular.

Leaves:
- *Shape.*—Cordiform.
- *Apex.*—Pointed.
- *Base.*—Rounded.
- *Margin.*—Teeth slightly irregular.
- *Length of teeth on margin.*—2-10 mm.
- *Shape of teeth on margin.*—Mostly straight with very few convex.
- *Texture* (*mature leaf*).—Upper surface: smooth and flat. Lower surface: glabrous with some pubescence at the primary vein junctions.
- *Size.*—Immature: Length: 6 cm at 10 days. Width: 6.5 cm at 10 days. Mature: Length: 15.5 cm at 4 weeks. Width: 15.5 cm at 4 weeks.
- *Color.*—Immature leaf: Upper surface: 2.5GY 7/10; anthocyanin 5R 5/10. Lower surface: 2.5GY 7/10; anthocyanin 5R 5/10. Mature leaf: Upper surface: 5GY 6/8. Lower surface: 5GY 5/6.
- *Venation.*—Pattern: primary veins on upper surface are slightly raised; veins on lower surface are raised. Color: Upper surface: 2.5GY 8/8. Lower surface: 2.5GY 6/10.
- *Petiolar sinus.*—U-shaped that are half to wide open. Lower later sinuses are deeply lobed and lyre shaped.
- *Petiole.*—Length: 11.7 cm. Diameter: 4.0 mm. Color: 2.5GY 7/8; anthocyanin 10R 5/8.

Floral Cluster:
- *General description and location.*—Mostly third node, range 2-4 nodes; 60% of clusters don't have shoulders.
- *Quantity of inflorescences per cluster.*—200.
- *Size.*—Length: 16.2 cm. Width: 14.2 cm (spread); 5.6 cm (hanging).
- *Peduncle length.*—2.5 cm.
- *Inflorescences.*—Hermaphroditic.
- *Stamens.*—Straight, 2.7mm.
- *Anthers.*—Small and nondescript.
- *Date of bloom.*—Start of bloom, May 5; and 100% bloom, May 15.
- *Pollen amount.*—Moderate.
- *Calyptra.*—5 segments with complete separation.
- *Calyptra color.*—5GY 5/6.

Fruit:
- *Time of year of commercial harvest and shipment.*—Late August.

*Cluster* (*primary bunches*).—General size: large (711 g tipped and 925 g not tipped). Length (without peduncle): 20.4 cm tipped and 26.5 cm not tipped. Width: 16.6 cm (hanging), 28.8 cm (spread). Density: medium. Peduncle: Length: 5.1 cm. Diameter: 5.7 mm. Color: 5GY 7/8. Number of berries per cluster: 92 tipped and 120 not tipped. Berry: Size: large (7.7 g). Diameter: 17.5 mm. Length: 32.9 mm. Shape: datiform. Uniformity: uniform. Brix content: 21.2 ° brix. Skin color: 5RP 3/2. Pedicel: Length: 8.1 mm. Diameter: 2.0 mm. Color: 2.5GY 8/6. Strength of attachment to berry: medium strength.

*Cluster* (*secondary bunches*).—General size: medium (167 g). Length (without peduncle): 8.5 cm. Width: 8.9 cm (hanging), 10.9 cm (spread). Density: medium. Peduncle: Length: 8.5 cm. Diameter: 4 mm. Color: 5GY 6/6. Number of berries per cluster: 38. Berry: Size: medium (4.4 g). Diameter: 16.8 mm. Length: 24.6 mm. Shape: mostly ovoid. Uniformity: medium to high. Brix content: 18.7 ° brix. Skin color: 5RP 3/2. Pedicel: Length: 7.3 mm. Diameter: 1.7 mm. Color: 2.5GY 7/6. Strength of attachment to berry: medium strength.

Berry Flesh:

*Color.*—2.5GY 8/4.

*Juice color.*—2.5Y 7/4.

*Juice production.*—High, 30% wt/wt.

*Thickness of skin.*—Medium.

*Flavor.*—Neutral.

*Fragrance.*—Neutral.

*Texture.*—Crisp.

*Seed.*—Seed rudiments not detectable.

*Use.*—Fresh table.

Disease and Insect Resistance: The disease and insect resistance of this cultivar is typical of its species.

What is claimed is:

1. A new and *Vitis vinifera* plant named 'Sheegene 101' as shown and described herein.

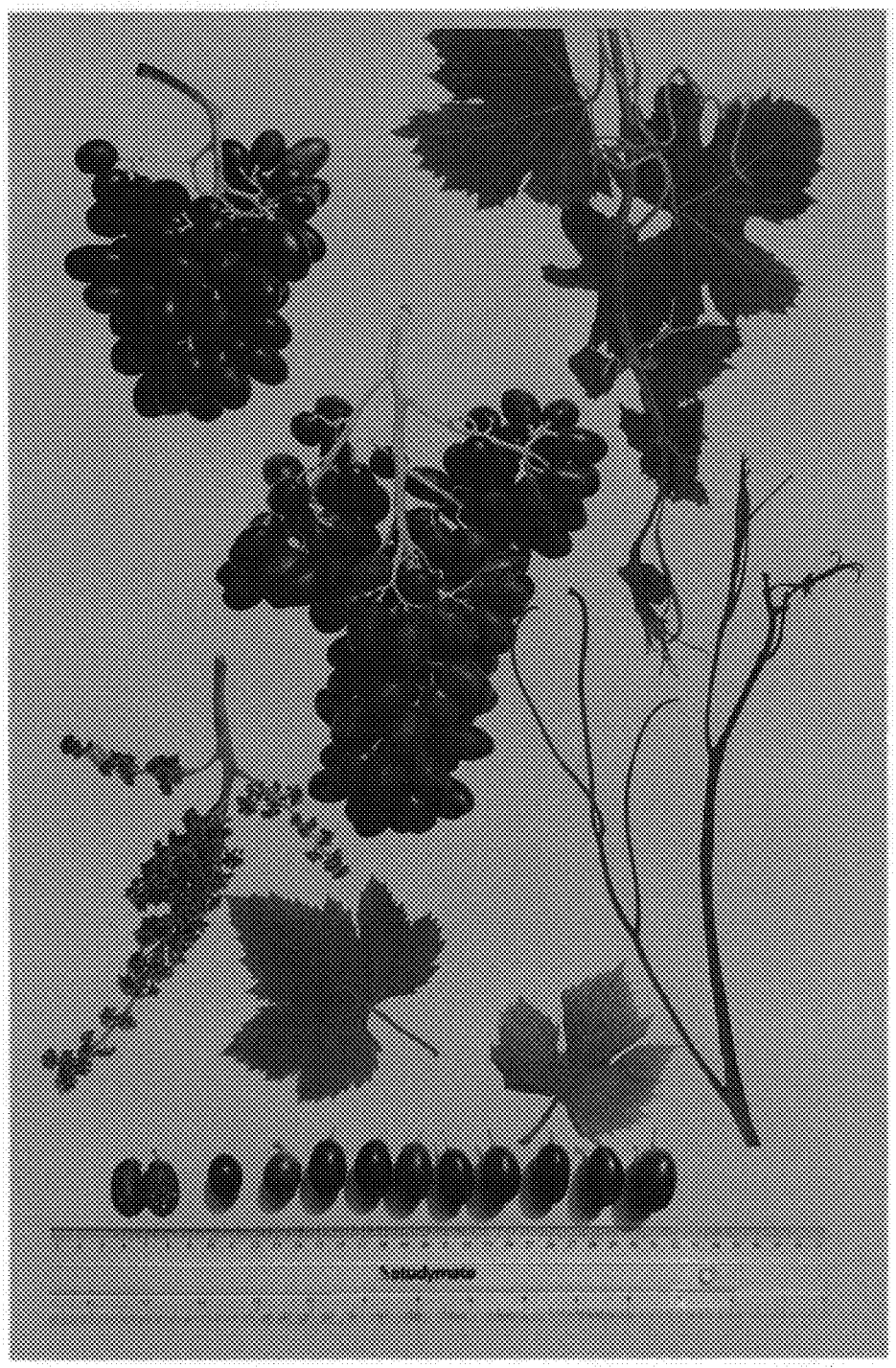

* * * * *